United States Patent [19]

Newman et al.

[11] Patent Number: 5,145,973
[45] Date of Patent: Sep. 8, 1992

[54] OXA-BICYCLIC POLYFUNCTIONAL COMPOUNDS AND PREPARATION THEREOF

[75] Inventors: Ronald S. Newman, North Brunswick, N.J.; St. Clair W. Greenidge, Brooklyn, N.Y.

[73] Assignee: Union Carbide Chemicals & Plastics Technology Corporation, Danbury, Conn.

[21] Appl. No.: 767,800

[22] Filed: Sep. 30, 1991

[51] Int. Cl.$^5$ .......................................... C07D 311/94
[52] U.S. Cl. ................................................. 549/397
[58] Field of Search ........................................ 549/397

[56] References Cited

U.S. PATENT DOCUMENTS

| | | | |
|---|---|---|---|
| 4,260,702 | 4/1981 | Schultz et al. | 549/397 |
| 4,721,725 | 1/1988 | Biller et al. | 514/412 |
| 4,762,845 | 8/1988 | Chu et al. | 514/312 |
| 4,788,315 | 11/1988 | Kawabata | 558/430 |
| 4,921,923 | 5/1990 | Zupancic et al. | 526/313 |
| 4,929,731 | 5/1990 | Kozikowski et al. | 546/97 |
| 4,954,502 | 9/1990 | Smith et al. | 514/253 |
| 4,957,921 | 9/1990 | Caprathe et al. | 514/252 |

FOREIGN PATENT DOCUMENTS 0343798 11/1989 European Pat. Off. .

*Primary Examiner*—Nicky Chan
*Attorney, Agent, or Firm*—J. F. Leightner

[57] ABSTRACT

Novel oxydiketones having the general structure:

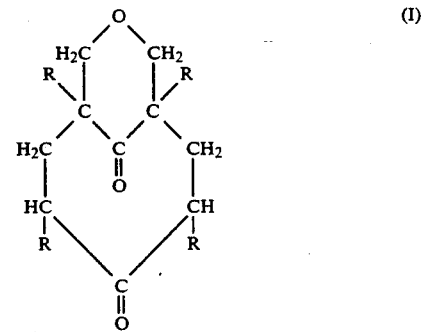

(I)

with R being alkyl groups of up to 12 carbon atoms and derivatives thereof having utility in the manufacture of various polymers and a process for their preparation are described.

3 Claims, No Drawings

OXA-BICYCLIC POLYFUNCTIONAL COMPOUNDS AND PREPARATION THEREOF

FIELD OF THE INVENTION

This invention relates to new oxa-bicyclic polyfunctional compounds and a method for their preparation. This invention also relates to the use of these new compounds in the formation of various types of polymers including polyesters, polyurethanes and polyamides.

SUMMARY OF THE INVENTION

The present invention provides a new class of bicyclic compounds having an eleven- or twelve-membered bicyclic nucleus, an ether oxygen as part of the bicyclic nucleus and at least two other functional groups bonded to respective carbons of the bicyclic nucleus. In one embodiment, the compounds of the invention are unsubstituted or substituted 1,3,5,7-tetraalkyl-9-oxa-bicyclo[5.3.1]-undecane-4,11-diones. For brevity, the diones are also referred to herein as the "oxydiketones." In another embodiment, the compounds of this invention are derivatives of the oxydiketones, such as corresponding 1,3,5,7-tetraalkyl-9-oxa-bicyclo-[5.3.1]-undecane-4,11-diols, -diamines and -diamides, as well as internal ester derivatives having a 12-membered bicyclic nucleus. The compounds of this invention have utility as chelating agents, especially the oxydiketones, and are also useful in the formation of various types of polymers such as polyesters, polyurethanes and polyamides.

The present invention also provides a method for preparing the compounds of the invention which method comprises reacting a ketone with formaldehyde under conditions effective to form the oxydiketone which, in turn, can be converted to the aforementioned diol, diamine, diamide, internal ester and other derivative products. By the term "derivative" as used herein is meant a compound or composition having a molecular weight not less than that of the oxydiketone parent compound.

DETAILED DESCRIPTION OF THE INVENTION

The oxydiketones of the invention have the following general Formula I:

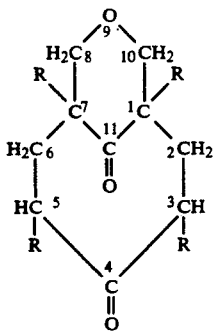

where each R is an alkyl group having from one to 12, and usually no more than six, carbon atoms. Preferably, R is a lower ($C_1$-$C_4$) alkyl group. It is to be understood that the alkyl groups may be linear or branched, and may be the same as or different from one another.

As is evident from Formula I, the four alkyl groups (R) are bonded to the respective carbon atoms in the 1, 3, 5 and 7 positions of the 11-membered bicyclic nucleus and the carbonyl groups are in the 4 and 11 positions. The hydrogen atoms bonded to the respective carbon atoms in the 3 and 5 positions are active hydrogen sites which can be reacted to form corresponding 3-monosubstituted and 3,5-disubstituted oxydiketones. The active C-3 and C-5 hydrogens undergo the well-known Michael addition reaction to form the corresponding 3-monosubstituted and 3,5-disubstituted oxydiketones including mixtures thereof. In forming such derivatives, suitable reactants are, for example, alpha, beta-unsaturated ketones, nitriles, carboxylic acids and esters, including allyl esters. Illustrative of such reactants are methyl vinyl ketone, acrylonitrile, ethyl acrylate, allyl acrylate and allyl methacrylate.

Among the novel specific compounds within the scope of general Formula I are:

1,3,5,7-tetramethyl-9-oxabicyclo[5.3.1]-undecane-4,11-dione;
1,3,5,7-tetraethyl-9-oxabicyclo[5.3.1]-undecane-4,11-dione;
1,3-dimethyl-5,7-diethyl-9-oxabicyclo[5.3.1]undecane-4,11-dione;
1,5-dimethyl-3,7-diethyl-9-oxabicyclo[5.3.1]undecane-4,11-dione;
1,3,5,7-tetrapropyl-9-oxabicyclo[5.3.1]-undecane-4,11-dione;
1,3,5,7-tetraisopropyl-9-oxabicyclo[5.3.1]undecane-4,11-dione;
1,3,5,7-tetrabutyl-9-oxabicyclo[5.3.1]-undecane-4,11-dione;
1,3,5,7-tetrapentyl-9-oxabicyclo[5.3.1]-undecane-4,11-dione;
1,3,5,7-tetrahexyl-9-oxabicyclo[5.3.1]-undecane-4,11-dione;
1,3,5,7-tetraoctyl-9-oxabicyclo[5.3.1]-undecane-4,11-dione;
1,3,5,7-tetranonyl-9-oxabicyclo[5.3.1]-undecane-4,11-dione;
1,3,5,7-tetradecyl-9-oxabicyclo[5.3.1]-undecane-4,11-dione;
1,3,5,7-tetraundecyl-9-oxabicyclo[5.3.1]-undecane-4,11-dione; and
1,3,5,7-tetradodecyl-9-oxabicyclo[5.3.1]-undecane-4,11-dione.

The oxydiketones encompassed by Formula I are produced by the method which comprises reacting formaldehyde with a ketone having the general formula:

where R is an alkyl group as defined above with respect to Formula I, under conditions effective to produce the oxydiketone. Several condensation, addition and dehydration reactions occur in forming the oxydiketones. The initial reaction between the ketone and formaldehyde forms a dihydroxy ketone which undergoes dehydration to a diisoalkenyl ketone which, in turn, reacts with additional dihydroxy ketone via a Michael addition to form a monocyclic dihydroxy diketone. The latter compound undergoes dehydration to form the oxydiketone of the invention. These various reactions can be, and usually are, effected in situ in a single reaction zone.

More particularly, the first reaction in the sequence is an aldol condensation between formaldehyde and ketone having general Formula II to form a dihydroxy ketone having the general formula:

The initial condensation reaction is effected in the presence of a base or an acid, with a weak base being preferred.

The dihydroxy ketone is then dehydrated using an acid or base to form water and a diisoalkenyl ketone having the formula:

The diisoalkenyl ketone and the dihydroxy ketone of Formula III are then reacted via a Michael addition using a base to catalyze the reaction to form a monocyclic dihydroxy diketone having the formula:

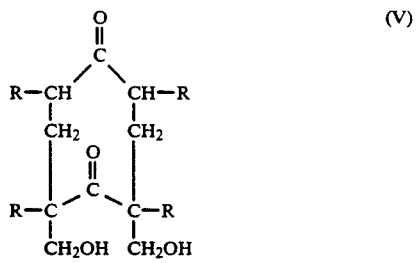

The dihydroxy diketone is then dehydrated using an acid or base to form an oxydiketone having Formula I.

As noted above, each of the above reactions can be effected in the presence of a base to catalyze the reactions. Up to about 5% by weight of base is provided, based upon the weight of the reactants charged. The base is preferably provided to the reaction as an aqueous solution. Inorganic and organic bases are suitable catalysts and include, for example, sodium hydroxide, sodium bicarbonate, potassium carbonate and triethylamine. A weak base, such as potassium carbonate, is preferred in the initial reaction between formaldehyde and ketone (II) to form the dihydroxy ketone (III). It is preferred that the base does not raise the pH of the aqueous reaction system above 10. A weak base is preferably employed in the initial reaction to produce the dihydroxy ketone because stronger bases can cause immediate dehydration of the newly formed dihydroxy ketone to the diisoalkenyl ketone (IV). When strong bases are used, an insufficient level of the dihydroxy ketone (III) may be present for addition to the diisoalkenyl ketone to form the monocyclic dihydroxy diketone (V). In the latter event, additional levels of dihydroxy ketone (III) can be added to the reaction system for reaction with the diisoalkenyl ketone intermediate to form the monocyclic dihydroxy diketone. The final dehydration reaction of the dihydroxy diketone (V) to the oxydiketones (I) of the invention is suitably effected in the presence of a strong base such as, for example, sodium hydroxide.

Alternatively, an acid may be used to catalyze some of the above-described reactions. Inorganic or organic acids may be used including sulfuric, hydrochloric, acetic and phosphoric acids. Acid levels up to about 5% by weight of the reactants can be employed.

A combination of acids and bases may also be employed in forming the oxydiketones. For example, the initial catalyst contained in the reaction mixture may be neutralized which effectively terminates the reaction. A second catalyst may then be employed to reinitiate the reaction. In a preferred embodiment, a weak base such as potassium carbonate is employed as a catalyst to initiate the reaction between the ketone and formaldehyde. When a desired conversion is achieved, potassium carbonate is neutralized with an acid. A second catalyst, such as sodium hydroxide, can then be employed as a catalyst to complete the reaction of the intermediates to form the oxydiketones of the invention.

The above-described series of reactions are preferably conducted under reflux, with by-product water being constantly removed. The continuous removal of water drives the equilibrium of the dehydration reaction to completion, resulting in higher yields of desired product. Triethylene glycol dimethyl ether can be added as a diluent to act as a pot boiler while the reaction mixture is being refluxed.

The reactions are conducted at temperatures of between 40° and 250° C., depending on the activity of the catalyst used. It is also desirable to react the ketone and formaldehyde with a sufficient amount of base such that an initial reaction temperature of about 70° to 100° C. is maintained for 4–6 hours. Subsequently, a higher reaction temperature can be employed until the reaction is completed.

The process of this invention can be effected continuously including reactions, neutralizations, distillations, crystalizations and drying. The process may also be effected as a batch process with a reaction time preferably in the range of 8 to 20 hours, the reaction being completed when the dihydroxy ketone has been consumed. The reaction contents are then cooled and the product crystals filtered and washed with triethylene glycol dimethyl ether, methanol or other suitable non-solvents. Any suitable method for separating and drying the filter cake is then employed. For example, the use of a vacuum dryer operating at about 60° C. and 5 mm Hg absolute pressure is suitably employed to separate and dry the product crystals from the non-solvent.

Inhibitors can also be added to the reaction mixture to prevent polymerization of alpha, beta-unsaturated ketones. Phenothiazine used, for example, at 100 parts per million by weight of total reactants charged, is effective in preventing such undesired polymerization.

As noted above, the compounds of the invention encompass derivatives of the oxydiketones. One class of derivatives are those in which the active hydrogen bonded to the C-3 and C-5 carbon atoms of the bicyclic nucleus are reactive via Michael additions. Suitable reactants for reaction with the reactive hydrogen include acrylonitrile and various alpha, beta unsaturated compounds such as methyl vinyl ketone, ethyl acrylate and allyl methacrylate. These reactants introduce substituents in the C-3 and/or C-5 positions of the bicyclic nucleus such as, for example, 2-cyanoalkyl and alkoxyethyl groups.

Other derivatives included within the scope of the invention have the following general Formula VI:

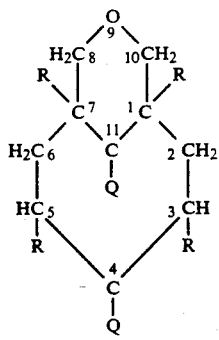

where:

R is an alkyl group as defined above with reference to Formula I;

Q is hydroxyl (—OH), primary amino (—NH$_2$), secondary amino (—NHR'), amido [—NHC(O)R'], ester [—OC—], cyanoethoxy (—OCH$_2$CH$_2$CN), cyanooxyalkylene [—O(C$_n$H$_{2n}$O)$_m$CH$_2$CH$_2$CN], or a urethane group [—OC(O)—NH—], where R' is an organic radical such as an alkyl group as above-defined with respect to the R group of Formula I, an arylalkyl group having from 7 to 12 carbon atoms, an aryl group having from 6 to 12 carbon atoms, or a cycloaliphatic group having from 5 to 12 carbon atoms; n has a value from 2 to 4 and m has a value from one to 50. The derivatives having Formula VI are prepared by various reactions well known to the art.

The preparation of the diol derivatives is accomplished by the hydrogenation of the oxydiketone. Typically, the addition of hydrogen is effected in the presence of a Raney catalyst such as Raney nickel or Raney cobalt or other catalysts such as platinum-on-alumina or palladium-on-carbon. Typical hydrogenation reaction conditions include a temperature from about 100° to 150° C. and a pressure from about 100 to about 200 (e.g., 150) psig.

The diol is then readily alkoxylated by reacting the diol in the presence of a catalyst and at least one alkylene oxide such as ethylene oxide, propylene oxide or mixtures thereof. Many catalysts for this reaction are known in the art, including potassium hydroxide, barium hydroxide, sodium methoxide and basic salts of alkaline earth metals.

The diamine derivatives are formed by the reductive amination of the oxydiketone. The reduction of the carbonyl is typically performed in the presence of a palladium, or platinum, on carbon catalyst. In forming compounds having Formula VI wherein Q is the primary amino group, —NH$_2$, the oxydiketone is reacted with ammonia in the form of ammonium hydroxide under a hydrogen atmosphere at a temperature ranging from 80°–120° C. and a pressure from about 100 to about 200 (e.g., 150) psig to form the diamine. The secondary amino group (—NHR') is introduced to the bicyclic nucleus in a manner similar to the reductive amination of the oxydiketone by reacting the oxydiketone with a primary amine. Thus, in forming the secondary diamines, a primary amine such as ethylamine, cyclohexyl amine or aniline is substituted for ammonia and the reaction is performed under similar conditions utilized to form the primary diamine derivatives.

Amide derivatives within the scope of Formula VI are formed from the corresponding diamine derivatives described above. This is accomplished by reaction of the diamine with carboxylic acids or esters thereof or acyl chlorides by well known reactions to form the corresponding amide; see, for example, Streitwiesser et al., *Introduction to Organic Chemistry*, 2nd Edition, MacMillian Publishing Co., New York, N.Y. (1981) pp. 753, 754.

The 1,3,5,7-tetraalkyl-4,11-di(2-cyanoethoxy)-9-oxabicyclo [5.3.1]undecane is readily formed through the reaction of the 1,3,5,7-tetraalkyl-9-oxa-bicyclo[5.3.1-.]undecane-4,11-diol and acrylonitrile via Michael addition. Similarly, 1,3,5,7-tetraalkyl-9-oxa-bicyclo-[5.3.1.]undecane-4,11-di[poly(oxyalkylene)nitrile] is formed by alkoxylation of the 1,3,5,7-tetraalkyl-9-oxa-bicyclo[5.3.1.]undecane-4,11-diol with an alkylene oxide in the presence of a catalyst. Potassium hydroxide is commonly used as catalyst in the reaction; see, for example, M. J. Schick, *Nonionic Surfactants*, Volume 1, Marcel Dekker, Inc., N.Y., N.Y (1967) pp. 28 to 41. The alkoxylated product can then be reacted with acrylonitrile to form the 1,3,5,7-tetraalkyl-9-oxa-bicyclo[5.3.1-.]undecane-4,11-di[poly-(oxyalkylene)nitriles].

The Baeyer-Villiger oxidation of the oxydiketones (I) forms internal ester structures. Oxygen atoms can be introduced into the bicyclic nucleus, alpha to one or both of the carbonyl groups of the oxydiketone. The reaction is carried out with various organic per-acids, e.g. perbenzoic, peracetic or monoperphthalic acid; see for example, Finar, I. L., Organic Chemistry, Vol I. Fundamental Principles, 6th Edition, Longman Publishing Company (1973) pp. 223, 224. Novel compositions formed from the Baeyer-Villiger oxidation include 1,3,5,7-tetra-methyl-9,12-dioxa-bicyclo[5.3.2.]dodecane-4,11-dione and 1,3,6,8-tetramethyl-5,10-dioxa-bicyclo-[6.3.1.]dodecane-4,12-dione.

The oxydiketones of the present invention can be used as chelating agents which are useful in sequestering metal ions. In addition, the novel compounds of the invention are also useful in the production of various polymers. For example, the diols formed from the hydrogenation of the oxydiketone are useful in polyurethane-forming formulations. Such formulations comprise polyether polyols, polyisocyanates and an amine catalyst and are well known to the art; see for example U.S. Pat. No. 4,067,828. The amine derivatives are useful in the preparation of various polyamides. For example, the diamine derivatives of the oxydiketone can be reacted with polycarboxylic acids such as adipic acid by methods also known to the art to form the corresponding polyamides. The diol derivatives of the invention can also be utilized in the formation of polyesters. For example, the diols can be reacted with the esters of dicarboxylic acids in transesterification reactions in the presence of known catalysts such as zinc acetate, lead acetate and glycol titanates to form polyesters.

The Examples which follow are presented for the purpose of illustrating the invention and are not to be construed as unduly limiting thereon. All parts and percentages are by weight unless otherwise specified.

EXAMPLE 1

Synthesis of 1.3.5.7-Tetramethyl-9-Oxa-Bicyclo[5.3.11]Undecane-4.11-Dione

A two-liter agitated reactor fitted with a 15 tray Oldshue column was charged with 344 grams of diethyl ketone. A burette was filled with 160 ml of a 37% formalin solution. The reactor was heated to 85° C. and the contents of the vessel were maintained at that temperature. The formalin was added to the reactor over a 15 minute period. The diethy 1 ketone/formalin solution was refluxed for five hours at 85° C. The reactor was then cooled and 2.53 grams of triethylamine was added to the reactor.

The reactor contents were once again heated to 85° C. and refluxed for three hours. Another five grams of triethylamine was added to the reactor. The reactor contents were refluxed for an additional four hours at 85° C. Fifty grams of overhead distillate was removed from the reactor. A caustic solution (10 grams of 50% sodium hydroxide and 250 grams of water) was then added to the reactor over a thirty minute period and the reactor temperature was increased to 100° C. Another 200 grams of overhead distillate was removed from the reactor over a five-hour period. Triethylene glycol dimethyl ether (250 grams) was added to the reactor as a diluent. The column was plugged and the reactor was shutdown. Another 100 ml of diethyl ketone was added to the reactor and after startup, an additional 70 grams of overhead distillate was removed from the reactor.

Approximately 450 grams of residue was found in the reactor. White crystals were recovered from the reactor bottoms and were analyzed by various techniques.

The normalized elemental analysis of the sample is tabulated below.

| Elemental Analysis | | |
| --- | --- | --- |
| | Measured | Actual |
| Weight % Carbon | 70.5 | 70.6 |
| Weight % Hydrogen | 9.6 | 9.2 |
| Weight % Oxygen | 19.9 | 20.2 |

The actual results are based upon the structure depicted by Formula I wherein each R is a methyl group. The correlation of the measured and actual results indicates that the crystalline product is 1,3,5,7-tetramethyl-9-oxabicyclo[5.3.1]-undecane-4,11-dione. This conclusion was confirmed by the NMR spectrum results presented below.

$^1$H-NMR(CDCl$_3$-d)$\delta$:0.91(s,6H),0.99(d,6H),1.2(d,2H),2.35 (m,2H),2.8(dd,2H),3.3(d,2H),3.7(d,2H)ppm.

$^{13}$C-NMR(CDCL$_3$-d)$\delta$:217.5, 214.7, 78.3, 50.3, 41.8, 40.8, 19.2, 18.9 ppm.

EXAMPLE 2

Alternate Synthesis of 1,3,5,7-Tetramethyl-9-Oxa-Bicyclo[5,3,1]Undecane-4,11-Dione An agitated 1-liter reactor, fitted with a 10-tray Oldshue column is charged with 172 grams of diethyl ketone and 20 grams of 47% aqueous potassium carbonate catalyst. The contents of the reactor are heated to 85° C. Over a two-hour period 240 grams of 50% low methanol formalin is added to the reactor. The reaction mixture is maintained at 85° C. until at least 90% conversion of the formaldehyde has been achieved. The reaction of formaldehyde and diethyl ketone requires about 12 hours to achieve the desired conversion. 250 grams of triethylene glycol dimethyl ether is added to the reactor and the reactor contents are neutralized with hydrochloric acid. Diethyl ketone/water is then stripped off at 200 mm Hg, the pressure being reduced such that the temperature in the reactor is maintained at less than 130° C. When the reactor temperature is 130° C. and the reactor pressure is 5 mm Hg, the reaction and distillation are both complete.

The reactor is then cooled to 50° C., atmospheric pressure is restored and 1 gram of 50% aqueous sodium hydroxide is added to the reactor. The ensuing reaction is maintained for about 12 hours to convert the 1,5-dihydroxy-2,4-dimethyl-3-pentanone to the above-captioned dione. The reactor is heated under vacuum (5 mm Hg absolute pressure) to strip off 100 grams of organic material. The contents of the reactor are rinsed with 500 ml of water and the slurry is filtered with the aid of a Buchner funnel. The recovered crystalline oxydiketone product is washed with a 50/50 methanol/water solution, and dried over magnesium sulfate.

EXAMPLE 3

Synthesis of 1.3.5.7-Tetramethyl-9-Oxa-Bicyclo[5.3.1]Undecane-4,11-Diol

An agitated 1-liter pressure reactor is charged with 23.8 grams of the dione made in Example 1, 200 ml of the solvent dioxane and 1 gram of Raney nickel. The contents of the reactor are heated to 120° C. and the reactor is pressurized to 150 psig with hydrogen. The reactor pressure is maintained at 150 psig by the addition of hydrogen to the reactor. When no additional hydrogen is required to maintain a constant reactor pressure, the reaction is complete. The reaction mixture is cooled and the reactor vented to atmospheric pressure. The Raney nickel is removed by settling. The reactor is heated to evaporate 150 ml of dioxane from the reactor. The remaining slurry of crystals in dioxane is filtered in a Buchner funnel. The crystals are washed in methanol and dried in an oven at less than 60° C. The crystalline product is a compound having Formula VI wherein Q is hydroxyl and each R is methyl.

EXAMPLE 4

Synthesis of a Polyester Based on 1.3.5.7-Tetramethyl-9-Oxa-Bicyclo5.3.11Undecane-4.11-Diol.

The diol of Example 3 (6.05 grams) is dissolved in 260 grams of neo-pentyl glycol. An agitated two-liter reactor provided with a distillation vessel, stirrer and thermometer is charged with 243 grams of the aforesaid diol/neo-pentyl glycol mixture, 399 grams of ethylene glycol, 780 grams of dimethyl terephthalate, and 0.526 grams of zinc acetate as catalyst. The mixture is heated so that the contents of the reactor increase in temperature from 25° to 140° C. over a period of four hours. The distillation of methanol is started when the reaction temperature reaches between 130° C. and 140° C. The reaction temperature of the mixture is then increased to 230° C. The reaction vessel is cooled thereby completing the ester exchange reaction from the dimethyl terephthalate to the polyester.

EXAMPLE 5

Synthesis of a Polyurethane Based on 1.3.5.7-Tetra-methyl-9-Oxa-Bicyclo5.3.1]Undecane-4,11-Diol The diol of Example 3 (0.5 grams) is dissolved in 59.5 grams of an ethylene glycol-adipate polyol (Hydroxyl No. 54) at 100° C. in a 250-ml stirred reactor. The diol- /ethylene glycol-adipate polyol mixture also contains 0.01 grams of 2,4-pentanedione, which acts as a reaction moderator.

In a second vessel 0.01 grams of pentanedione is added to 22.5 grams of diphenyl methylene diisocyanate at room temperature.

The pentanedione/diphenyl methylene diisocyanate mixture is added over a five minute period to the polyol mixture. The reaction temperature is maintained at 100° C. and the contents are vigorously stirred throughout the reaction. A castable polyurethane is formed after about one-half hour of reaction.

EXAMPLE 6

Synthesis of 1.3.5.7-Tetramethyl-9-Oxa-Bicyclo5.3.1]-Undecane-4,11-Diamine

A mixture of 4.76 grams of the dione made in Example 1 and 200 ml of dioxane are stirred in the presence of 0.05 grams of 5% palladium-on-carbon catalyst in a 1-liter pressure reactor. The mixture is placed under a hydrogen atmosphere at ambient conditions. Saturated ammonium hydroxide (5 ml) is added to the mixture and the mixture is heated to 100° C. Sufficient hydrogen is added to maintain 150 psig pressure in the reactor. Hydrogen is continuously added to maintain 150 psig pressure on the reactor. The reaction is complete when no further addition of hydrogen is required.

The reactor is first cooled and then the hydrogen pressure is vented from the reactor and the catalyst is removed by filtration. Ammonia and 185 ml of dioxane are evaporated from the solution. One hundred ml of water is added and the remaining slurry of crystals are filtered using a Buchner funnel. The crystals are rinsed in cold methanol and dried in an oven at less than 60° C. The crystalline product is a compound having Formula VI wherein Q is —NH$_2$ and R is methyl.

EXAMPLE 7

Synthesis of 1,3,5,7-Tetramethyl-9,12-Dioxa-Bicyclo-[5.3.2]Dodecane-4,11-Dione and

1,3,6,8-Tetramethyl-5,10-Dioxa-Bicyclo[6.3.1]-Dodecane-4,12-Dione via Baeyer-Villiger Oxidation The dione of Example 1 (2.38 grams) is dissolved in 100 grams of ethyl acetate at 40° C. in a stirred 500 ml reactor with a fitted still. The contents of the reactor are purged with nitrogen.

Over a two-hour period, 3.2 grams of a 25% solution of peracetic acid in ethyl acetate is added drop-wise to the reactor. The reaction is conducted at 40° C. for twelve hours. At the conclusion of the reaction, a sufficient amount of aqueous sodium bicarbonate is added to neutralize the acid. Ninety ml of the ethyl acetate/water azeotrope is stripped off overhead by the still. The contents of the reactor are then cooled and 100 ml of water is added. The slurry is filtered and water washed. The internal ester products of the subject example are dried over magnesium sulfate.

EXAMPLE 8

Synthesis of Polyamide Based on 1,3,5,7-Tetramethyl-9-Oxa-Bicyclo[5.3.1]-Undecane-4,11-Diamine The diamine of Example 6 (1.2 grams) is dissolved in 115.42 grams of hexamethylene diamine at 50° C. in a stirred 1-liter reactor fitted with a still. Ninety grams of water is added to the mixture. While stirring the solution, 146 grams of powdered adipic acid is added. The contents of the reactor are heated to 250° C. under pressure for four hours. The reactor is slowly vented to condense water vapor. When about 105 grams of water condensate has been collected, molten polyamide is discharged from the reactor.

EXAMPLE 9

Synthesis of 3,5-Di(2-Cyanoethyl)-1,3,5,7-Tetramethyl-9-Oxa-Bicyclo[5.3.1]Undecane-4,11-Dione The dione of Example 1 (2.38 grams) is dissolved in 20 ml of dioxane in a 250-ml stirred reactor fitted with a still. One hundred grams of water is added to the mixture which is heated to 30° C. Sufficient sodium hydroxide (50% solution) is added to bring the pH of the solution to between 9 and 10. Acrylonitrile (10.6 grams) is added drop-wise over eight hours. After an additional two hours, sufficient phosphoric acid is added to neutralize the sodium hydroxide. Excess acrylonitrile is stripped off under vacuum. 100 ml of dioxane is added to the reactor and any polymer formed in the reactor is removed by filtration. About 200 ml of liquid is stripped from the filtrate to leave a slurry of crystals. After adding 100 ml of water, the crystals are separated by filtration, washed with water and dried at a temperature below 60° C. The crystalline product comprises a compound having Formula I where R is methyl, except that the hydrogen atoms bonded to the C-3 and C-5 positions of the bicyclic nucleus are 2-cyanoethyl groups.

We claim:

1. A 1,3,5,7-tetraalkyl-9-oxa-bicyclo[5.3.1.]undecane-4,11-dione having the formula:

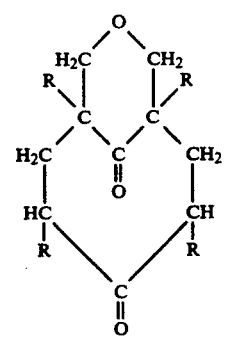

where R is an alkyl group having from one to 12 carbon atoms.

2. A compound as defined in claim 1 wherein R is an alkyl group having no more than six carbon atoms.

3. A compound as defined in claim 1 wherein R is methyl.

* * * * *